United States Patent [19]

Pimentel

[11] Patent Number: 5,741,489
[45] Date of Patent: Apr. 21, 1998

[54] PASSIVELY ADMINISTERED ANTIBODY THAT ENHANCES FEED CONVERSION EFFICIENCY

[75] Inventor: Julio Pimentel, Buford, Ga.

[73] Assignee: Anitox Corporation, Buford, Ga.

[21] Appl. No.: 653,604

[22] Filed: May 24, 1996

[51] Int. Cl.⁶ ............................................. A61K 39/395
[52] U.S. Cl. ........................ 424/157.1; 424/158.1; 424/163.1; 424/164.1; 424/804; 530/388.26; 530/389.1
[58] Field of Search ................. 424/130.1, 157.1, 424/158.1, 163.1, 164.1, 802, 803, 804; 530/388.26, 389.1

[56] References Cited

U.S. PATENT DOCUMENTS 5,494,660  2/1996  Hunter et al.
5,585,098  12/1996  Coleman.

FOREIGN PATENT DOCUMENTS

WO 9496474 A   3/1994   WIPO.

OTHER PUBLICATIONS

Erhard, M. H. et al. Berliner und Munchener Tierarztliche Wochenscrift 106 (11): 383–387, Nov. 1993.

*Primary Examiner*—Frank C. Eisenschenk
*Assistant Examiner*—Evelyn Rabin
*Attorney, Agent, or Firm*—Oblon, Spivak, McClelland, Maier & Neustadt, P.C.

[57] ABSTRACT

A method for increasing feed conversion efficiency in mammals, such as swine, wherein the mammal is fed a diet containing an antibody produced using the enzyme urease as the antigen.

8 Claims, No Drawings

PASSIVELY ADMINISTERED ANTIBODY THAT ENHANCES FEED CONVERSION EFFICIENCY

BACKGROUND OF THE INVENTION

1. Field of the Invention

A feed additive which increases feed conversion efficiency in animals.

2. Discussion of the Background

In the animal industry, antibiotics are commonly used to prevent infections, improve animal performance and treat infectious diseases. Alternative methods to replace antibiotics for improving performance have not been commercially available.

At the present time, most of the antibiotics used in animal production are different from therapeutics used in humans. However, the emergence of multi-resistant bacteria to any antibiotic used in animals removes the possibility of that antibiotic ever being used as a therapeutic agent in humans. The continuous use of antibiotics as preventative agents or growth promoters also causes problems with drug residues in animal produce and an increasing problem of environmental pollution. Studies have indicated that as much as 75% of the administered antibiotic may be excreted via the urine and feces back into the environment (Addison, 1984).

It has been demonstrated that hens injected with a foreign antigen will develop specific antibodies and deposit them in the egg yolk. Antibodies specific to Salmonella, E. coli, and other types of bacteria are produced by the animal when orally challenged (Ricke et al, 1988; Neighbor et al, 1991). When these antibodies are administered to the animal and it is subsequently challenged with the bacteria, the antibodies prevent infection (Bartz et al, 1980; Sherman et al, 1983; Tacket et al, 1988; Kuhlmann et al, 1988; Yolker et al, 1988; Shmidt et al, 1989; Wiedemann et al, 1990; Hatta et al, 1993a and 1993b; Kuroki et al, 1993). Increased growth of chicks and poults obtained from hens injected with jackbean urease was reported by Pimentel et al, 1991 and Pimentel and Cook (1988).

There are at least two possible mechanisms by which antibodies prevent infection. Antibodies have been reported to decrease the number of bacteria in the gastro-intestinal tract by preventing the bacteria from attaching to the intestinal wall. Antibodies may also decrease bacterial numbers by binding to specific receptors on the intestinal wall or the bacteria itself thus preventing bacterial multiplication (Ishida et al, 1992). Either mechanism of action of antibodies in preventing disease would overcome the deficiencies of bacterins. In addition, antibodies do not result in the emergence of resistant strains of bacteria or pose the threat of leaving undesirable residues in animal produce.

SUMMARY OF THE INVENTION

A method for increasing feed conversion efficiency in a mammal comprising feeding a mammal a diet containing an effective amount of an antibody which binds to urease.

DESCRIPTION OF THE PREFERRED EMBODIMENTS

The present invention relates to a method for increasing feed conversion efficiency in animals by augmenting their feed with antibodies which bind to urease. The preferred antigen for obtaining the antibodies is jackbean urease which is commercially available from Sigma Chemical Co. We have found that mammals and, in particular, swine show enhanced feed conversion efficiency when raised for three to four consecutive weeks on a diet containing anti-urease antibodies, at a dose of 25 to 500 mg of antibody extract per ton of feed, preferably 25 to 100 mg/ton. On the average, feed conversion in swine is enhanced 9 to 15 points, or more. Antibody extract is described in Example 2. Alternatively, the eggs can be dried and mixed with feed without first isolating the antibodies, as described in Example 7. Cows and sheep also grow with enhanced feed conversion if raised on feed containing anti-urease antibodies.

Poultry feed containing anti-urease antibodies enhances the growth rate and feed conversion efficiency of poultry, including chickens and turkeys.

The production of anti-urease antibodies can be accomplished by injecting animals, such as rodents or rabbits, with urease and collecting the blood serum which contains the antibody. However, this procedure is costly and highly invasive to the animal.

A general method for producing antibodies which is non-invasive and more economically feasible is known. It has been observed that eggs contain 50–150 mg of various antibodies. When a hen is injected with a particular antigen, 10–20% of the antibody isolated from the eggs are specific to that antigen (Losch et al, 1986; Kuhlmann et al, 1988; Burdsall et al, 1990; Gassmann et al, 1990). The immunoglobulin class of antibodies produced in eggs has been identified as IgY which is similar to IgG produced in mammals (IgG). Egg yolk antibodies are absorbed by piglets in a similar manner to homologous pig antibodies. Wiedemann et al (1990) observed that active antibodies were found throughout the distal jejunum in 8 week-old piglets fed lyophilized egg yolk containing antibodies. The activity of antibodies was improved when the animals were supplied with sodium bicarbonate which reduced the acidity in the stomach. Antibodies have been reported to be more resistant to degradation by gastric acidity when they are contained in the spray-dried whole egg, as compared to purified spray-dried antibodies. Yokoyama et al (1993) reported active antibodies from the stomach through the ileum two hours after the piglets (28 day-old) were orally fed chicken antibodies. In a related study, Ishida et al (1992) demonstrated that 8 and 18 months old mice had a significantly suppressed growth of intestinal Enterobacteriaceae when fed milk from hyperimmunized cows that were injected with human gut bacteria. Chicken antibodies can further be protected from stomach acidity and pepsin hydrolysis by encapsulating them within liposomes (Shimuzu et al. 1993).

Previous research on the effectiveness of chicken antibodies in preventing bacterial infections in swine has been reported. In in vitro studies, Jungling et al (1991) observed that egg yolk antibodies were effective in decreasing the adhesion of enterotoxigenic E. coli onto isolated pig enterocytes. In in vivo tests, spray-dried egg yolk extracts containing antibodies against E. coli prevented colibacillosis in newborn piglets and calves (Yokoyama et al, 1992 and 1993, Erhard et al, 1993) and decreased the number of days that pigs were with diarrhea (Kellner et al, 1994).

Although chicken antibodies in general are known to protect the recipient against bacterial infections, no antibody has been shown to increase feed conversion efficiency, i.e., transforming a given amount of feed into more body weight gain. The present invention provides a method of using an antibody against an enzyme (urease) which is present in the gastro-intestinal tract to obtain increased feed utilization (feed conversion efficiency) and body weight gain in mammals.

Other features of the invention will become apparent in the course of the following descriptions of exemplary embodiments which are given for illustration of the invention and are not intended to be limiting thereof.

EXAMPLE 1

A. This example illustrates the preparation of a specific antibody against urease. At 17 weeks of age (placing hens into cages), hens were injected with 0.2 mg of urease type II-C (Sigma Chemical Company). The inoculum was prepared by dissolving the enzyme in 0.2 ml phosphate buffered saline (PBS; pH 7.3) and 0.2 ml complete Freund's adjuvant. The antigen preparation was injected intramuscularly into two sites, 0.2 ml in each (right and left) pectoralis muscle. A total of 0.4 ml of antigen preparation per hen was administered. A second injection was administered 5–6 week following the initial injection (about 50% egg production). In the second antigen preparation, incomplete Freund's adjuvant was used instead of complete Freund's adjuvant. Hens were re-injected with the antigen preparation every two months or when the antibody titer was determined to be low. Antibody titer was determined every four weeks by ELISA. Eggs containing the specific antibody were collected 1 week after the second injection. Hens were maintained in an isolated room in order to minimize outside contamination. They were under a vaccination program similar to commercial settings.

B. In another experiment the hens were injected with antigen three times, which increases the average yield of anti-urease in the eggs.

EXAMPLE 2

Antibody was purified as suggested by Kwan, et al (1991). Briefly, one volume of egg yolk of Example 1A. was mixed with 9 volumes of distilled water and left to sit overnight at 4° C. Then the aqueous portion was centrifuged at 4000 rpm for 10 minutes, and filtered through a cheesecloth in order to remove any excess fat. Liquid was frozen for freeze drying at a future time. After freeze drying, the antibody was heat treated (one hour at 50°–70° C.) to improve stability. The antibody activity was determine by an ELISA. Before running the ELISA, protein concentration in the egg extract was determined by the Bradford procedure and adjusted to 1 mg/ml.

EXAMPLE 3

The procedure for the ELISA was as follows:

1. Plates were coated with 100 ul urease solution (10 ug/ml) in carbonate buffer. The exact antigen concentration was determined with a checkerboard titration. The plates were incubated at 4° C. overnight prior to blocking with 1.5% bovine serum albumin for 4 hours at room temperature.
2. 100 ul of the 1 mg protein/ml egg extract was added to each well and the plates incubated at room temperature for 30 minutes.
3. Plates were washed with PBS-Tween 20 solution. 100 ul of a 1:20,000 dilution of rabbit-anti chick IgG conjugated to horseradish peroxidase was added to each well. The plates were incubated at room temperature for 30 minutes. The exact enzyme-antibody conjugate concentration was determined with a checkerboard titration.
4. Plates were washed with the PBS-Tween and 100 ul of TMB substrate was added to each well. The plates were incubated at room temperature for 15 minutes.
5. The reaction was stopped with 100 ul of 2M sulfuric acid.
6. Plates were read at 455 nm in an ELISA plate reader.
7. Titer was determine as the inverse of the last dilution in which O.D. of the immunized egg was similar to the un-immunized control (O.D.<0.100).

EXAMPLE 4

This study illustrates the effect of adding purified antibody to the feed of mammals. Two experiments were conducted with starter (6-week old) piglets. Control and antibody treated feed was supplied for four weeks. Antibody dose was 50 mg/kg diet. Feed and water were supplied at libitum. Feed intake and body weight were measured weekly, feed conversion was calculated weekly and expressed as feed intake/body weight gain. The results from those two experiments are shown on tables 1 through 4.

TABLE 1

| Antibody concentration | (exp 1) Body weight gain (kg/week) | | | | |
|---|---|---|---|---|---|
| (mg/kg feed) | 1 | 2 | 3 | 4 | Total |
| 0 | 3.90 | 3.97 | 5.27 | 5.17 | 18.31 |
| 50 | 4.73 | 4.69 | 5.22 | 4.90 | 19.54 |

TABLE 2

| Antibody concentration | (exp 1) feed conversion | | | | |
|---|---|---|---|---|---|
| (mg/kg feed) | 1 | 2 | 3 | 4 | Total |
| 0 | 1.74 | 1.49 | 1.94 | 1.93 | 1.79 |
| 50 | 1.31 | 1.74 | 1.84 | 1.68 | 1.65 |

TABLE 3

| Antibody concentration | (exp 2) Body weight gain (kg/week) | | | | |
|---|---|---|---|---|---|
| (mg/kg feed) | 1 | 2 | 3 | 4 | Total |
| 0 | 3.89 | 4.00 | 4.93 | 5.50 | 18.32 |
| 50 | 4.39 | 4.39 | 4.84 | 5.24 | 18.86 |

TABLE 4

| Antibody concentration | (exp 2) feed conversion | | | | |
|---|---|---|---|---|---|
| (mg/kg feed) | 1 | 2 | 3 | 4 | Total |
| 0 | 1.34 | 1.89 | 1.94 | 2.08 | 1.84 |
| 50 | 1.15 | 1.73 | 1.93 | 2.08 | 1.74 |

EXAMPLE 5

An experiment was conducted with weaned pigs. Pigs were fed either a control diet or an antibody mixture for 6 weeks. Fifty mg antibody extract was mixed with 1 kilogram fine ground corn and then mixed with one metric ton feed. Feed and water were supplied ad libitum. Body weight was measured at 2, 4 and 6 weeks. Results are shown in table 5.

TABLE 5

| Days | daily gain (gr) weight | | % improvement over control |
|---|---|---|---|
| | control | antibody | |
| 1-14 | 163 | 203 | 24 |
| 1-28 | 340 | 362 | 7 |
| 1-42 | 414 | 461 | 11 |

EXAMPLE 6

This example illustrates the preparation of spray dried egg containing a urease specific antibody. Antibody-containing eggs were homogenized and then spray dried. Antibody activity is unaffected when eggs are spray dried, as compared to a freeze dried standard. The parameters used to spray dry are: inlet temperature/outlet temperature 140° C./70° C., blower at 50% capacity, compressor at 75% and pump at 30% capacity. All those parameters were obtained in a laboratory scale Virtis Spray Dryer. In order to sterilize and to improve the stability of the antibody (increase shelf life), spray dried egg was incubated at 60° C. for 7 days. We have run antibody samples and found that this process does not decrease the antibody activity.

Since spray dried product contained fat, one gram of product was mixed with 10 ml phosphate buffered saline (PBS) followed by 10 ml of chloroform. That suspension was mixed thoroughly and then centrifuged at 4000 rpm to separate the protein from the lipid fraction. The protein content of the supernatant was determined by the Bradford procedure using bovine gamma-globulin as protein standard. The extract was diluted with PBS to 1 mg protein/ml prior to antibody activity and titer determination as described in example 1.

EXAMPLE 7

Two experiments were conducted with pigs from 6 weeks of age through market weight (200 lbs body weight). The antibody this time was not isolated from the egg yolk, instead whole egg (white and yolk) was homogenized and spray dried (example 6). The amount of dried egg needed to equal the activity of the purified antibody was 250 mg/kg of diet. Results are shown in tables 6 and 7.

TABLE 6

| | 17 week body weight (kg) | Gain 0-17 week (kg) | Total feed intake (kg) | Feed conversion |
|---|---|---|---|---|
| control | 93.95 | 83.49 | 217.7 | 2.61 |
| antibody | 99.74 | 89.42 | 223.5 | 2.50 |

TABLE 7

| | 15 week body weight (kg) | Gain 0-15 week (kg) | Total feed intake (kg) | Feed conversion |
|---|---|---|---|---|
| control | 97.00 | 81.32 | 209.2 | 2.58 |
| antibody | 98.37 | 82.77 | 198.4 | 2.40 |

EXAMPLE 8

Dried egg containing antibody was prepared as in example 4. Pigs were maintained in the experiment for 16 weeks, from starter period through market weight. The results are present in table 8.

TABLE 8

| | Total Gain (kg) | Total feed intake (kg) | Feed conversion |
|---|---|---|---|
| control | 1290 | 3470 | 2.69 |
| antibody | 1367 | 3624 | 2.65 |

EXAMPLE 9

This study illustrates the antibody stability on the spray dried whole egg when stored at room temperature and at high temperature. Spray dried egg samples (0.5-1.0 gr.) were placed in small vials (4 ml) capped and stored at room temperature (21° C.) or in an incubator at 37° C. Weekly antibody activity was measured from vials kept at those temperatures and the activity was compared to a sample that was kept at 0° C. The results are present in table 9.

TABLE 9

| Temperature | % antibody activity remaining weeks | | | | | | | |
|---|---|---|---|---|---|---|---|---|
| | 0 | 1 | 2 | 3 | 6 | 9 | 12 | 18 |
| 0 C. | 100 | 100 | 100 | 100 | 100 | 100 | 100 | 100 |
| 21 C. | 100 | 98 | 100 | 98 | 96 | 94 | 95 | 85 |
| 35 C. | 100 | 91 | 100 | 99 | 97 | 100 | 94 | 95 |

Obviously, numerous modifications and variations of the present invention are possible in light of the above teachings. It is therefore to be understood that within the scope of the appended claims, the invention may be practiced otherwise than as specifically described herein.

REFERENCES

1. Addison, J. B. (1984) antibiotics in sediments and run off waters from feedlots. Residues Reviews 92:1-28.

2. Bartz, C. R., R. H. Conklin, C. B. Tunstall and J. H. Steele (1980). Prevention of murine rotavirus infection with chicken egg yolk immunoglobulins. J. Infect. Dis. 142:439-441.

3. Blanco, J. E., M. Blanco, J. Blanco, L. Rioja and J. Ducha (1994). Serotypes, toxins and antibiotic resistance of Escherichia coli strains isolated from diarrhoeic and healthy rabbits in Spain. Vet. Microb.38:193-201

4. Burdsall, H. H., M. Banik, M. E. Cook (1990). Serological differentiation of three species of Armillaria and Lentinula by enzyme-linked immunosorbent assay using immunized chickens as a source of antibodies. Mycologia 84: 415-423.

5. Erhard, M. H., J. Kellner, J. Eichelberger and U. Losch (1993). New aspects in oral immunoprophylaxis for the prevention of infectious diarrhea of newborn calves—a field study with specific egg antibodies. Berl. Munch. Tierarztl. Wschr.106:383–387.

6. Gassmann, M., P. Thommes, T. Weiser and U. Hubscher (1990). Efficient production of chicken egg antibodies against a conserved mammalian protein. Faseb J. 4:2528–2532.

7. Hatta, H; K. Tsuda, S. Akachi, M. Kim and T. Yamamoto (1993a). Productivity and some properties of egg yolk antibody (IgY) against human rotavirus compared with rabbit IgG. Biosci. Biotech. Biochem. 57:450–454.

8. Hatta, H., K. Tsuda, S. Akachi, M. Kim, T. Yamamoto and T. Ebina (1993b). Oral passive immunization effect of anti-human rotavirus IgY and its behavior against proteolytic enzymes. Biosci. Biotech. Biochem. 57:1077–1081.

9. Ishida, A. Y. Yoshikai, S. Murosaki, C. Kubo, Y. Hidaka, and K. Nomoto (1992). Consumption of milk from cows immunized with intestinal bacteria influences age-related changes in immune competence in mice. J. Nutrition 122:1875–1883.

10. Jungling, A., V. Wiedemann, R. Kuhlmann, M. Erhard, P. Schmidt and U. Losch (1991). Chicken egg antibodies for prophylaxis and therapy of infectious intestinal diseases. J. Vet. Med 38:373–381.

11. Kellner, J. M. H. Erhard, M. Renner and U Losch (1993). a field trial of the treatment of diarrhea in piglets with specific egg antibodies. Jahrgang (49) Jan 94(1) 31–34.

12. Kuhlmann, R., V. Wiedemann, P. Schmidt, R. Wanke, E. Linckh and U. Losch (1988). Chicken egg antibodies for prophylaxis and therapy of infectious intestinal diseases. I.—Immunization and antibody determination. J. Vet. Med. B. 35:610–616.

13. Kuroki, M., Y. Ikemori, H. Yokoyama, R. Peralta, F. Icatlo and Y. Kodama (1993). Passive protection against bovine rotavirus-induced diarrhea in murine model by specific immunoglobulins from chicken egg yolk. Vet. Micro. 37:135–146.

14. Kwan, L. E. Li-Chan, N. Helhig and S. Nakai (1991). Fractionation of water soluble and insoluble components from egg yolk with minimum use of organic solvents. J. Food. Sci. 56:1537–1541.

15. Losch, U., I. Strainer, R. Wanke and L. Jargons (1986). The chicken egg, an antibody source. J. Vet. Med. B. 33:609–619.

16. Neighbor, N. K., J. K. Skeeles, J. N. Beasley and D. L. Kreider (1991). Use of an enzyme-linked immunosorbent assay to measure antibody levels in turkey breeders hens, eggs, and progeny following natural infection or immunization with a commercial Bordetella avium bacterin. Avian Dis. 35:315–320.

17. Niisten, R., N.London, A. van den Bogaard and E. Stobberingh (1993). Antibiotic resistance of enterobacteriaceae isolated from the fecal flora of fattening pigs. The Veterinary Quarterly 15:153–157

18. Pimentel, J. L. and M. E. Cook (1988). Improved growth in the progeny of hens immunized with jackbean urease. Poultry Sci. 67:434–439.

19. Pimentel, J. L., J. Jonnson and M. E. Cook (1991). Increased growth of chicks and poults obtained from hens injected with jackbean urease. Poultry Sci. 70:1842–1844.

20. Ricke, S. C., D. M. Schaefer and M. E. Cook (1988). Differentiation of ruminal bacterial species by enzyme-linked immunosorbent assay using egg yolk antibodies from immunized hens. Appl. Environ. Microb. 54:596–599.

21. Schmidt, P. ,V. Wiedemann, R. Kuhlmann, R. Wanke, E. Linckh and U. Losch (1989). Chicken egg antibodies for prophylaxis and therapy of infectious diseases. II.—In vitro studies on gastric and enteric digestion of egg yolk antibodies specific against pathogenic Escherichia coli strains. J. Vet. Med. B. 36:619–628.

22. Shimuzu, M., Y. Miwa, K. Hashimoto and A. Goto (1993) Encapsulation of chicken egg yolk immunoglobulin Y (IgY) by liposome. Biosci. Biotech. Biochem. 57:1445–1449.

23. Sherman, D. M., S. D. Acres, P. L. Sadowski, J. A. Springer, B. Bau.,T. J. G. Raybould and C. C. Muscoplat (1983). Protection of calves against fatal enteric colibacillosis by orally administered Escherichia coli K99—specific monoclonal antibody. Infect. Immun. 42:653–658.

24. Tacit, C. O., G. Losonsky, H. Link, Y. Hoang, P. Guesry and M. Levine (1988). Protection by milk immunoglobulin concentrate against oral challenge with enterotoxigenic Escherichia coli. N. Engl. J. Med. 318:1240–1243.

25. Kellner, J. M. H. Erhard, M. Renner and U Losch (1993). a field trial of the treatment of diarrhea in piglets with specific egg antibodies. Jahrgang (49) Jan 94(1) 31–34.

26. Wiedemann, V., R. Kuhlmann, P. Schmidt, W. Erhardt and U. Losch (1990). Chicken egg antibodies for prophylaxis and therapy of infectious intestinal diseases. III.—In vivo tenacity test in piglets with artificial jejunal fistula. J. Vet. Med. B. 37:163–172.

27. Yokoyama, H., R. Peralta, R. Diaz, S. Sendo, Y. Ikemori and Y. Kodana (1992). Passive protective effect of chicken egg yolk immunoglobulins against experimental enterotoxigenic Escherichia coli infection in neonatal piglets. Infect. Immunity 60:998–1007.

28. Yokoyama, H., R. Peralta, S. Serdo, Y. Ikemori (1993). Detection of passage and absorption of chicken egg yolk immunoglobulins in the gastrointestinal tract of pigs by the use of enzyme-linked immunosorbent assay and fluorescent antibody testing. Am. J. Vet. Res. JY:867–872.

29. Yolker, R. H., F. Leister, S. B. Wee, R. Miskuff and V. Vonderfecth (1988) Antibodies to rotaviruses in chicken's eggs: a potential source of antiviral immunoglobulin suitable for human consumption. Pediatrics 81:291–295.

We claim:

1. A method for increasing feed conversion efficiency in swine comprising: feeding swine a diet containing an effective amount of an antibody which binds to urease wherein said diet is provided from starter period through market weight.

2. The method of claim 1 wherein the urease is jackbean urease.

3. The method of claim 1 wherein the feed contains 25 to 100 mg of purified antibody per ton of feed.

4. A method of claim 1 wherein the antibody was produced in eggs.

5. The method of claim 4 wherein the antibody was produced in chicken eggs.

6. The method of claim 4 wherein the eggs have been dried and added to the feed.

7. The method of claim 3 wherein said mammal is fed said feed for at least four consecutive weeks.

8. The method of claim 6 wherein the eggs have been freeze dried and heated at 50°–70° C. to improve antibody stability.

* * * * *